United States Patent
Sivasankar et al.

(10) Patent No.: US 7,317,141 B2
(45) Date of Patent: Jan. 8, 2008

(54) TRANSCRIPTIONAL ACTIVATORS INVOLVED IN ABIOTIC STRESS TOLERANCE

(75) Inventors: Sobhana Sivasankar, Urbandale, IA (US); Timothy G. Helentjaris, Tucson, AZ (US); Deping Xu, Johnston, IA (US); Anna Lyznik, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/386,655

(22) Filed: Mar. 22, 2006

(65) Prior Publication Data

US 2006/0162027 A1 Jul. 20, 2006

Related U.S. Application Data

(63) Continuation-in-part of application No. 11/114,672, filed on Apr. 26, 2005, now Pat. No. 7,253,000.

(60) Provisional application No. 60/565,430, filed on Apr. 26, 2004.

(51) Int. Cl.
*C12N 15/82* (2006.01)

(52) U.S. Cl. .................................................... 800/289

(58) Field of Classification Search ................... None
See application file for complete search history.

(56) References Cited

U.S. PATENT DOCUMENTS

| | | | |
|---|---|---|---|
| 2003/0233680 A1* | 12/2003 | Thomashow et al. | 800/289 |
| 2004/0019927 A1* | 1/2004 | Sherman et al. | 800/278 |
| 2004/0034888 A1* | 2/2004 | Liu et al. | 800/289 |
| 2004/0045049 A1 | 3/2004 | Zhang et al. | |
| 2004/0191910 A1 | 9/2004 | Shinozaki et al. | |
| 2004/0214272 A1* | 10/2004 | La Rosa et al. | 435/69.1 |
| 2005/0097638 A1 | 5/2005 | Jiang et al. | |

FOREIGN PATENT DOCUMENTS

| | | |
|---|---|---|
| CA | 2 408 972 A1 | 5/2003 |
| WO | 2005047516 A2 | 5/2005 |

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Fowler, S.G., et al.; "*Arabidopsis* transcriptome profiling indicates that multiple regulatory pathways are activated during cold acclimation in addition to the CBF cold response pathway"; Plant Cell (2002) 14(8):1675-1690.
Gilmour, S.J., et al.; "Overexpression of the *Arabidopsis* CBF3 Transcriptional Activator Mimics Multiple Biochemical Changes Associated with Cold Acclimation"; Plant Physiol. (2000) 124(4):1854-1865.
Gilmour, S.J., et al.; "*Arabidopsis* transcriptional activators CBF1, CBF2, and CBF3 have matching functional activities"; Plant Mol. Biol. (2004) 54(5):767-781.
Haake, V., et al.; "Transcription Factor CBF4 is a Regulator of Drought Adaptation in *Arabidopsis*"; Plant Physiol. (2002) 130(2):639-648.
Jaglo, K.R., et al.; "Components of the *Arabidopsis* C-Repeat/Dehydration-Responsive Element Binding Factor Cold-Response Pathway Are Conserved in *Brassica napus* and Other Plant Species"; Plant Physiol. (2001) 127 (3):910-917.
Jaglo-Ottensen, K.R., et al.; "*Arabidopsis* CBF1 Overexpression Induces COR Genes and Enhances Freezing Tolerance"; Science (1998) 280:104-106.
Stockinger, E.J., et al.; "Transcriptional adaptor and histone acetyltransferase proteins in *Arabdopsis* and their interactions with CBF1, a transcriptional activator involved in cold-regulated gene expression"; Nucleic Acids Res. (2001) 29(7):1524-1533.
Stockinger, E.J., et al.; "*Arabidopsis thaliana* CBF1 encodes an AP2 domain-containing transcriptional activator that binds to the C-repeat/DRE, a cis-acting DNA regulatory element that stimulates transcription in response to low temperature and water deficit"; PNAS (1997) 94:1035-1040.
Thomashow, M.F., et al.; "Role of the *Arabidopsis* CBF transcriptional activators in cold acclimation"; Physiol. Plantarum (2001) 112(2):171-175.
Thomashow, M.F., et al.; "So What's New in the Field of Plant Cold Acclimation? Lots!"; Plant Physiol. (2001) 125(1):89-93.
Zarka, D.G., et al.; "Cold Induction of *Arabidopsis* CBF Genes involves Multiple ICE (Inducer of CBF Expression) Promoter Elements and a Cold-Regulatory Circuit That is Desensitized by Low Temperature"; Plant Physiol. (2003) 133(2):910-918.
Kizis, D., et al.; "Role of AP2/EREBP transcription factors in gene regulation during abiotic stress"; FEBS (2001) 498:187-189.

* cited by examiner

*Primary Examiner*—David H. Kruse
*Assistant Examiner*—Vinod Kumar

(57) ABSTRACT

The present invention provides compositions and methods for regulating expression of nucleotide sequences in a plant. Compositions comprise novel nucleic acid sequences encoding a transcription factor involved in modulating gene expression in response to abiotic stress such as cold or drought. Methods for expressing the nucleic acid sequence in a plant and improving cold and/or drought tolerance of plants are also provided.

2 Claims, 5 Drawing Sheets

```
(1)  1                10                  20              30                40               50               60               70              83
(1) PKKPAGRKKFRETRHH EYRGVRRRN-SGKWVCEVREPNKK-TRIWLGTFQTAEMAARAHDVAALALRGR-SACLNFADS AWRL
(1) PKRPAGRTKFKETRHP LYRGVRRRGRLGQWVCEVRMRGAQGYRLWLGTFTTAEMAARAHDSAVLALLDR-AACLNFADS AWRM
(1) PKRPAGRTKFRETRHP VYRGVRRGPAGRWVCEVREPNKK-SRIWLGTFATPEAAARAHDVAALALRGR-AACLNFADS ARLL
(1) PKRPAGRTKFRETRHP VFRGVRRGSAGRWVCEVRMPGRRGCRLWLGTEDTAEAAARAHDAAMLALAGAGACCLNFADS AWLL
(1) PKRPAGRTKFRETRHP VYRGVRRRG  AGRWVCEVRVPNKKGSRIWLGTF  TAEMAARAHDVAALALRGR  AACLNFADS AWRL
```

Figure 1. Alignment of domains of, from top, the Arabidopsis CBF3, Rye CBF31, maize CBF1 and maize CBF2 polypeptides, and a consensus sequence.

FIGURE 2
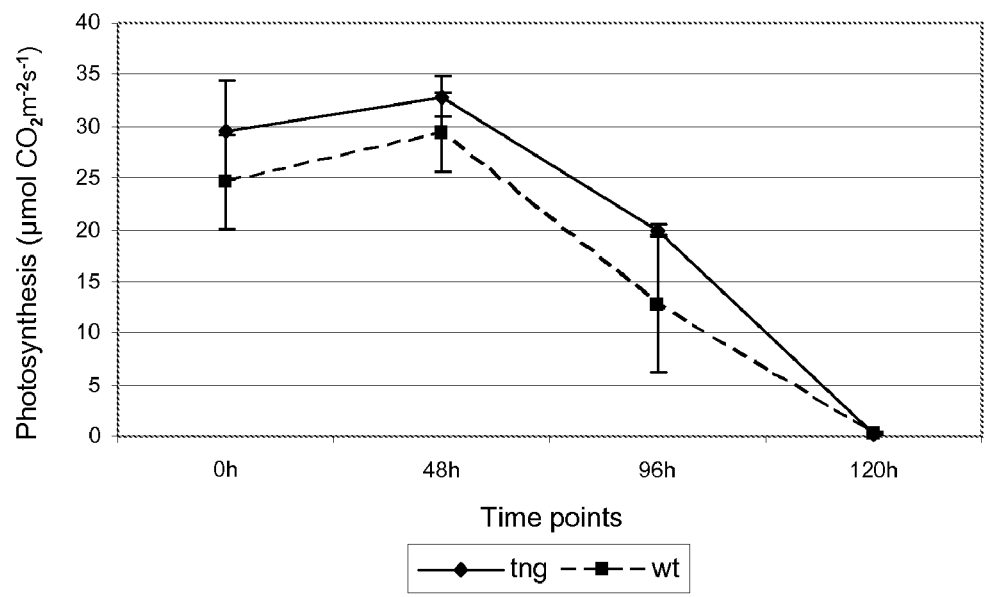
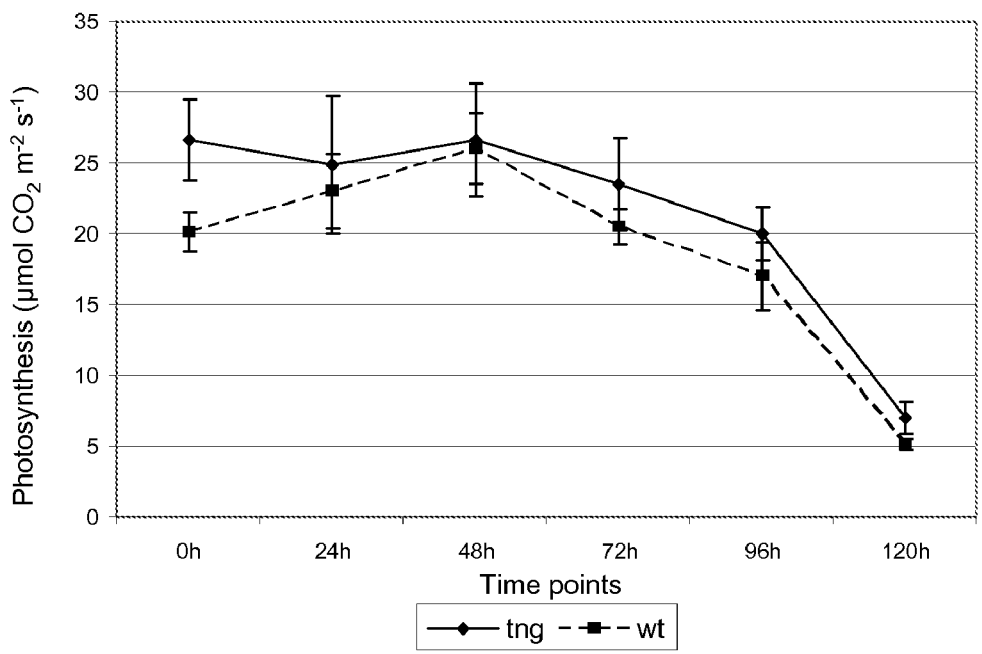

FIGURE 4

| Accession Number | Sequence Description | Fold Change |
|---|---|---|
| AJ012301.1 | Proline-rich protein [Zea mays] | 67.10 |
| U43034.2 | Permease 1 [Zea mays] | 63.96 |
| AF068119.1 | Beta-amylase [Zea mays] | 63.43 |
| AY372244.1 | Cellulose synthase catalytic subunit 10 [Zea mays] | 40.92 |
| af244678_1 | Glutathione S-transferase GST 13 [Zea mays] | 28.45 |
| af232008_1 | Beta-glucosidase aggregating factor precursor [Zea mays] | 26.26 |
| AF126054.1 | Rop3 small GTP binding protein [Zea mays] | 23.84 |
| AF326483.1 | NOD26-like membrane integral protein ZmNIP1-1 [Zea mays] | 23.34 |
|  | Maize homolog of AY224518.1, Senescence-associated protein-like protein [Oryza sativa (japonica cultivar-group)] | 19.87 |
| p47917 | O-methyltransferase [Zea mays] | 14.88 |
|  | Maize homolog of P09886, Chloroplast small heat shock protein [Pisum sativum] | 14.67 |
| AF326494 | Plasma membrane integral protein ZmPIP2-4 [Zea mays] | 13.71 |
|  | Maize homolog of XM_550380.1, Putative serine/threonine protein phosphatase 2A [Oryza sativa (haponica cultivar-group)] | 12.44 |
| AJ251019.1 | Polyamine oxidase [Zea mays] | 11.74 |
| AF326504.1 | Tonoplast membrane integral protein ZmTIP3-1 [Zea mays] | 11.51 |
| AF326492.1 | Plasma membrane integral protein ZmPIP2-2 [Zea mays] | 11.14 |
| AY758275.1 | Mitochondrial small heat shock protein [Zea mays] | 10.37 |
| AF332170_1 | Alpha-expansin 2 [Zea mays] | 10.03 |
| AJ223470 | Phytase [Zea mays] | 10.00 |
| AJ401274.1 | Peroxidase [Zea mays] | 9.88 |
| AY488135.1 | Allene oxide synthase [Zea mays] | 9.85 |
| X69961.1 | H2B histone [Zea mays] | 9.77 |
| AY197773.1 | Fructokinase 2 [Zea mays] | 9.20 |
| AF332169_1 | Alpha-expansin [Zea mays] | 9.09 |
| U66105 | Phospholipid transfer protein [Zea mays] | 8.86 |
| U45857 | Cytosolic glyceroldehyde-3-phosphate dehydrogenase GAPC4 [Zea mays] | 8.73 |
| L05934.1 | Catalase [Zea mays] | 8.20 |
| L77912_1 | Phenylalanine ammonia-lyase [Zea mays] | 7.81 |
| af236374_1 | Hypersensitive-induced response protein [Zea mays] | 7.27 |
|  | Maize homolog of AP005844.3, Putative cytosolic monodehydroascorbate reductase [Oryza sative (japonica cultivar-group)] | 6.93 |
| X74217.1 | Beta-glucosidase [Zea mays] | 6.66 |
| X54076 | 18kDa heat shock protein [Zea mays] | 6.20 |
| X65931.1 | Glutamine synthaetase [Zea mays] | 5.99 |
|  | Maize homolog of AP004018.3, Putative late embryogenesis abundant domain-containing protein [Oryza sativa (japonica cultivar-group)] | 5.56 |
|  | Maize homolog of XM_467861.1, Putative early-responsive to dehydration stress protein [Oryza sativa (japonica cultivar-group)] | 5.40 |

FIGURE 4

| Accession Number | Sequence Description | Fold Change |
|---|---|---|
|  | Maize homolog of XM_475961.1, Putative late embryogenesis abundant protein [Oryza sativa (japonica cultivar-group)] | 5.11 |
| AY005818 | Hemoglobin [Zea mays subsp. mays] | 4.52 |
| AF050128.1 | Cell wall invertase Incw2; beta-fructosidase [Zea mays] | 4.47 |
| AY243801.1 | Aquaporin [Zea mays] | 4.36 |
| AF439723.1 | Methionine synthase [Zea mays] | 4.35 |
| AY675582.1 | RuBisCo subunit binding-protein beta subunit [Zea mays] | 4.14 |
|  | Maize homolog of NM_121121.2, Embryonic abundant protein-like [Arabidopsis thaliana] | 4.13 |
| AY188755.1 | Atypical receptor-like kinase MARK [Zea mays] | 3.93 |
|  | Maize homolog of AP005636.2, Dehydration-responsive protein-like [Oryza sativa (japonica cultivar-group)] | 3.86 |
|  | Maize homology of NM_194841.1, Putative thaumatin-like protein [Oryza sativa (japonica cultivar-group)] | 3.86 |
| AF232008_1 | Beta-glucosidase aggregating factor precursor [Zea mays] | 3.68 |
| AY243803.1 | Tonoplast water channel [Zea mays] | 3.54 |
| U89897 | Golgi associated protein se-wap41 [Zea mays] | 3.43 |
| af311223_1 | C2H2 zinc-finger protein [Zea mays] | 3.24 |
| af077337_1 | Heat shock protein 101; 101 kDa heat shock protein [Zea mays] | 3.17 |
| Af223412_1 | Kinesin-like calmodulin binding protein [Zea mays] | 3.02 |
| AB042270 | Histidine kinase 1 [Zea mays] | 2.92 |
| L35913.1 | Dehydrin [Zea mays] | 2.88 |
| L33244.1 | Sucrose synthase 2 [Zea mays] | 2.68 |
| AY279009.1 | Caffeoyl CoA 3-O-methyltransferase [Zea mays] | 2.65 |
| AY532724.1 | Chitinase [Zea mays subsp. parviglumis] | 2.59 |
| AB035645.1 | Ferredoxin [Zea mays] | 2.48 |
| AF323175.1 | Inositol-3-phosphate synthase [Zea mays] | 2.46 |
| X89813 | Calcium-binding protein [Zea mays] | 2.36 |
| af271384_1 | Putative tryptophan synthase alpha [Zea mays] | 2.32 |
| AF288075.1 | Diphoosphonucleotide phosphatase 1 [Zea mays] | 2.17 |
| af178951_1 | Voltage-dependent anion channel protein 1b [Zea mays] | 2.12 |
| AY722707.1 | Putative salt-inducible protein kinase [Zea mays] | 2.09 |
| AF178952_1 | Voltage-dependent anion channel protein 2 [Zea mays] | 2.07 |
| D63954.1 | Fatty acid desaturase [Zea mays] | 2.03 |

TRANSCRIPTIONAL ACTIVATORS INVOLVED IN ABIOTIC STRESS TOLERANCE

This is a continuation-in-part application of U.S. Ser. No. 11/114,672, filed Apr. 26, 2005 now U.S. Pat. No. 7,253,000, which claims priority to and incorporates by reference U.S. provisional application 60/565,430, filed Apr. 26, 2004.

FIELD OF THE INVENTION

The present invention relates to the field of plant molecular biology, more particularly to regulation of gene expression in plants.

BACKGROUND OF THE INVENTION

Stresses to plants may be caused by both biotic and abiotic agents. For example, biotic causes of stress include infection with a pathogen, insect feeding, parasitism by another plant such as mistletoe, and grazing by ruminant animals. Abiotic stresses include, for example, excessive or insufficient available water, temperature extremes, synthetic chemicals such as herbicides, and excessive wind. Yet plants survive and often flourish, even under unfavorable conditions, using a variety of internal and external mechanisms for avoiding or tolerating stress. Plants' physiological responses to stress reflect changes in gene expression.

Insufficient water for growth and development of crop plants is a major obstacle to consistent or increased food production worldwide. Population growth, climate change, irrigation-induced soil salinity, and loss of productive agricultural land to development are among the factors contributing to a need for crop plants which can tolerate drought. Drought stress often results in reduced yield. In maize, this yield loss results in large part from plant failure to set and fill seed in the apical portion of the ear, a phenomenon known as tip kernel abortion.

Low temperatures can also reduce crop production. A sudden frost in spring or fall may cause premature tissue death.

Physiologically, the effects of drought and low-temperature stress may be similar, as both result in cellular dehydration. For example, ice formation in the intercellular spaces draws water across the plasma membrane, creating a water deficit within the cell. Thus, improvement of a plant's drought tolerance may improve its cold tolerance as well.

CBF genes (for C-repeat/DRE binding factor) encode proteins which may interact with a specific cis-acting element of certain plant promoters. (U.S. Pat. Nos. 5,296,462 and 5,356,816; Yamaguchi-Shinozaki, et al., The Plant Cell 6:251-264 (1994); Baker, S. S., et al., Plant Mol. Biol. 24:701-713 (1994); Jiang, C., et al., Plant Mol. Biol. 30:679-684 (1996)) The cis-acting element is known as the C-repeat/DRE and typically comprises a 5-base-pair core sequence, CCGAC, present in one or more copies.

CBF proteins comprise a CBF-specific domain and an AP2 domain and have been identified in various species, including *Arabidopsis* (Stockinger et al., Proc. Natl. Acad. Sci. 94:1035-1040, 1997; Liu et al., Plant Cell 10:1391-1406, 1998; *Brassica napus, Lycopersicon esculentum, Secale cereale,* and *Triticum aestivum* (Jaglo et al., Plant Phys. 127:910-917, 2001) and *Brassica juncea, Brassica oleracea, Brassica rapa, Raphanus sativus, Glycine max,* and *Zea mays* (U.S. Pat. No. 6,417,428).

Overexpression of CBF in plants has been shown to improve tolerance to drought, cold, and/or salt stress (Jaglo-Ottosen et al., Science 280:104-106, 1998; Kasuga et al., Nature Biotechnology 17:287-291, 1999; Hsieh et al., Plant Phys. 129:1086-1094, 2002; Hsieh et al., Plant Phys. 130: 618-626, 2002; Dubouzet et al., Plant J. 33:751-763, 2003). While CBF transcription factors may be useful in transgenic approaches to regulate plant response to stress, constitutive expression of CBF results in negative pleiotropic effects. Controlled expression of CBF in selected tissues and/or under stress conditions is of interest.

SUMMARY OF THE INVENTION

Compositions and methods for regulating gene expression in a plant are provided. Compositions comprise isolated polynucleotides encoding a transcription factor involved in modulating gene expression in response to cold and/or drought. Further compositions of the invention comprise a polynucleotide of the sequence set forth in SEQ ID NO: 1 or SEQ ID NO: 3, and operable fragments of each. The compositions of the invention further comprise polynucleotides having at least 85% identity to either of the complete sequences set forth in SEQ ID NO: 1 and SEQ ID NO: 3, and polynucleotides which hybridize under stringent conditions to SEQ ID NO: 1 or to SEQ ID NO: 3 or to a complement of either.

In one embodiment of the invention, a DNA construct comprises an isolated polynucleotide of the invention operably linked to a promoter sequence, wherein the promoter is capable of driving expression of the nucleotide sequence in a plant cell. The promoter sequence may be heterologous to the linked nucleotide sequence. In some embodiments, said promoter sequence is inducible by an exogenous agent or environmental condition. In some embodiments, said promoter initiates transcription preferentially in certain tissues or organs.

Also provided are expression cassettes comprising said DNA construct; vectors containing said expression cassette; transformed plant cells, transformed plants, and transformed seeds comprising the novel sequences of the invention.

Further embodiments comprise methods for expressing a polynucleotide of the invention in a plant. The methods comprise stably incorporating into the genome of a plant cell an expression cassette comprising a promoter sequence operably linked to a polynucleotide of the invention, wherein the promoter is capable of initiating transcription of said polynucleotide in a plant cell. Certain embodiments of the present invention comprise methods for modulating the development of a transformed plant under conditions of stress.

BRIEF DESCRIPTION OF THE DRAWINGS

FIG. 1 provides an alignment of several CBF polypeptides: AtCBF3 (SEQ ID NO: 11-12), RyeCBF31 (SEQ ID NO: 10), ZmCBF1 (SEQ ID NO: 3-4), ZmCBF2 (SEQ ID NO: 1-2). The boxed region outlined by the dotted line is the CBF-specific domain, and boxed region outlined by the solid line is the AP2 domain.

FIG. 2 provides photosynthesis data for transgenic and non-transgenic plants as described in Example 12.

FIG. 4 is a table of 66 genes upregulated more than two-fold in maize plants expressing UBI::ZmCBF1.

DETAILED DESCRIPTION OF THE INVENTION

Figure 3:
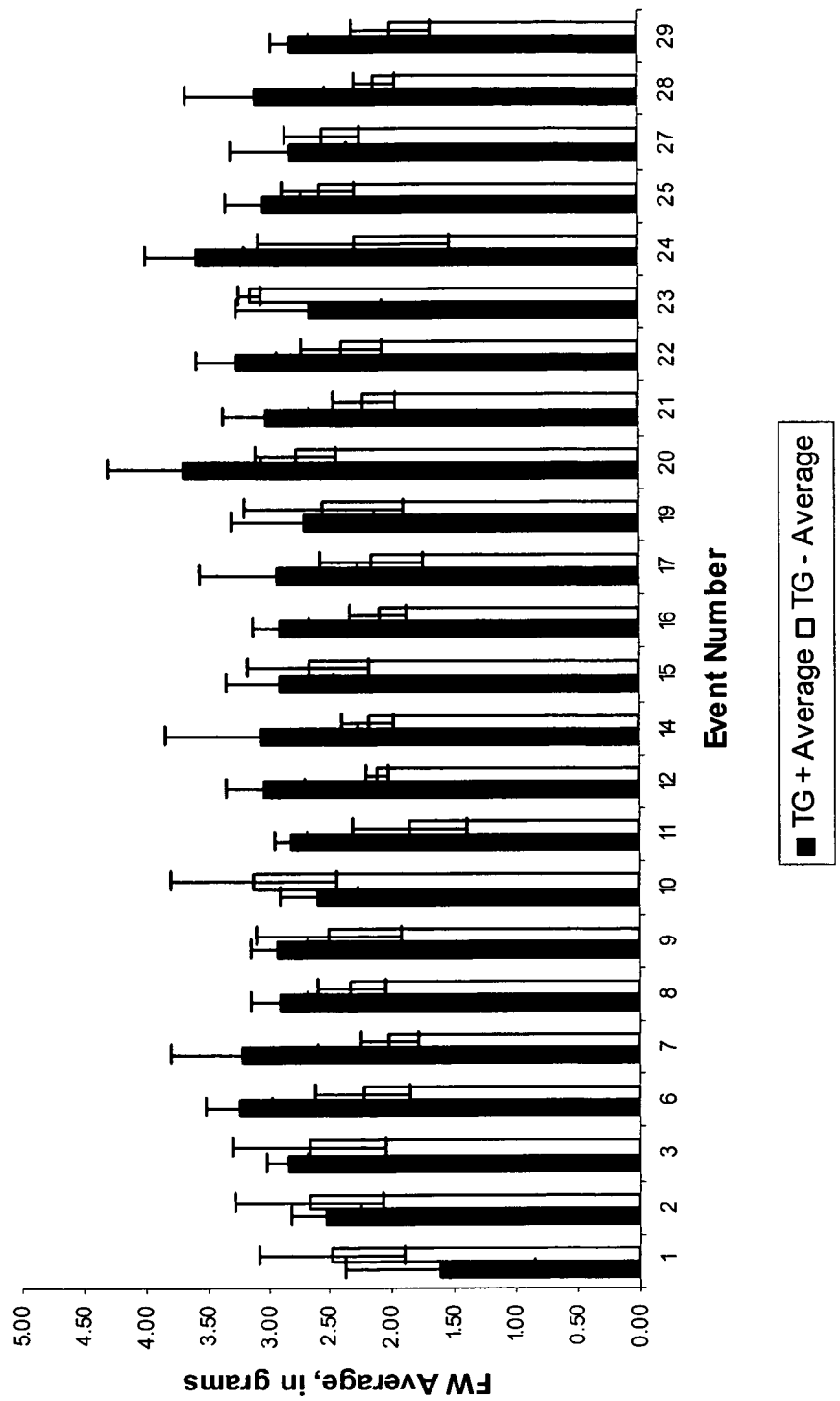
FIG. 3 provides average fresh weight under chilling stress for transgenic and non-transgenic seedlings as described in Example 10.

In accordance with the invention, isolated polynucleotides are provided that encode transcription initiation factors involved in stress-induced gene expression, particularly drought or cold stress.

By "recombinant expression cassette" or "expression cassette" is meant a nucleic acid construct, generated recombinantly or synthetically, comprising a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the expression cassette portion of an expression vector includes, among other sequences, a promoter and a nucleic acid to be transcribed.

By "heterologous nucleotide sequence" is intended a sequence that is not naturally occurring with another sequence. For example, a nucleotide sequence encoding a transcription factor may be heterologous to the promoter sequence to which it is operably linked. Further, the coding sequence and/or the promoter sequence may be native or foreign to the plant host.

By "operable fragment" is meant a truncated or altered form of a particular polynucleotide or polypeptide which is sufficient to perform or provide the relevant function. For example, where the goal is to interfere with gene function, a truncated form of a polynucleotide may be sufficient for purposes of co-suppression or anti-sense regulation. Where the goal is to initiate transcription, a promoter or transcription factor which is less than the full length known, or which comprises minimal internal deletions or alterations, may still function appropriately. Promoter sequences provided, or one or more fragments thereof, may be used either alone or in combination with other sequences to create synthetic promoters. In such embodiments, the fragments (also called "cis-acting elements" or "subsequences") confer desired properties on the synthetic promoter.

By "promoter" is intended a region of DNA upstream from the start of transcription and involved in recognition and binding of RNA polymerase and other proteins to initiate transcription. A promoter usually comprises a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. Thus a promoter region may be further defined by comprising upstream regulatory elements such as those responsible for tissue and temporal expression of the coding sequence, enhancers, and the like. In the same manner, the promoter elements which enable expression in the desired tissue can be identified, isolated, and used with other core promoters.

A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells, such as *Agrobacterium* or *Rhizobium*. Examples of promoters under developmental control include tissue-preferred promoters, which preferentially initiate transcription in certain tissues, such as leaves, roots, or seeds, and those promoters driving expression when a certain physiological stage of development is reached, such as senescence. Promoters which initiate transcription only in certain tissue are referred to as "tissue-specific." A "cell-type-preferred" promoter primarily drives expression in certain cell types in one or more organs, for example, vascular tissue in roots or leaves. An "inducible" or "repressible" promoter is a promoter which is under environmental control. Examples of environmental conditions that may effect transcription by inducible promoters include anaerobic conditions or the presence of light. Certain promoters are induced by unfavorable environmental conditions, for example, rab17 (exemplified by SEQ ID NO: 5; see also Busk et al., Plant J 11:1285-1295 (1997)), rd29A (exemplified by SEQ ID NO: 6; see also GenBank D13044 and Plant Cell 6:251-264, 1994), rip2 (exemplified by SEQ ID NOS: 7 and 8; see also GenBank L26305 and Plant Phys. 107(2):661-662 (1995)), and mlip15 (exemplified by SEQ ID NO: 9; see also GenBank D63956; Mol. Gen. Gen. 248(5):507-517 (1995). Tissue-specific, tissue-preferred, cell-type-preferred, and inducible promoters are members of the class of "non-constitutive" promoters. A "constitutive" promoter is a promoter which is active in all or nearly all tissues, at all or nearly all developmental stages, under most environmental conditions.

It is recognized that to increase transcription levels, enhancers can be utilized in combination with promoter regions to increase expression. Enhancers are known in the art and include the SV40 enhancer region, the 35S enhancer element, and the like.

A "subject plant" or "subject plant cell" is one in which genetic alteration, such as transformation, has been effected as to a gene of interest, or is a plant or plant cell which is descended from a plant or plant cell so altered and which comprises the alteration. A "control" or "control plant" or "control plant cell" provides a reference point for measuring changes in the subject plant or plant cell.

A control plant or control plant cell may comprise, for example: (a) a wild-type plant or plant cell, i.e., of the same genotype as the starting material for the genetic alteration which resulted in the subject plant or subject plant cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or subject plant cell; (d) a plant or plant cell genetically identical to the subject plant or subject plant cell but which is not exposed to conditions or stimuli that would induce expression of the gene of interest; or (e) the subject plant or subject plant cell itself, under conditions in which the gene of interest is not expressed.

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome.

A polynucleotide may be single- or double-stranded, depending on the context, and one of skill in the art would recognize which construction of the term is appropriate.

The Zea mays sequences of the invention can be used to isolate corresponding sequences from other organisms, particularly from other plants, more particularly from other monocotyledonous plants. Methods such as PCR, hybridization, and the like can be used to identify such sequences based on their similarity to a sequence set forth herein. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequences of the invention. For example, an entire sequence disclosed herein, or one or more portions thereof, may be used as a probe capable of specifically hybridizing to corresponding sequences. To achieve specific hybridization under a variety of conditions, such probes include sequences that are distinctive and are at least about 10 nucleotides in length. The well-known process of polymerase chain reaction (PCR) may be used to isolate or amplify additional sequences from a chosen organism or as a diagnostic assay to determine the presence of corresponding sequences in an organism. Hybridization techniques include hybridization screening of plated DNA libraries (either plaques or colonies; see, for example, Sambrook et al., supra; see also Innis et al., eds., (1990) *PCR Protocols, A Guide to Methods and Applications*, Academic Press). Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.) and Ausubel et al., eds. (1995) *Current Protocols in Molecular Biology*, Chapter 2 (Greene Publishing and Wiley-Interscience, New York).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are target-sequence-dependent and will differ depending on the structure of the polynucleotide. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringency may also be adjusted with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See also Sambrook et al. (1989) *Molecular Cloning: A Laboratory Manual* (2d ed., Cold Spring Harbor Laboratory Press, Plainview, N.Y.). Thus, isolated sequences that retain the function of the invention and hybridize under stringent conditions to the sequences disclosed herein, or to their complements, or to fragments of either, are encompassed by the present invention. Such a sequence will usually be at least about 85% identical to a disclosed sequence. That is, the identity of sequences may range, sharing at least about 85%, 86%, 87%, 88%, 89%, 90%, 91%, 92%, 93%, 94%, 95%, 96%, 97%, 98%, 99% or more sequence identity.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Nat. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the GCG® Wisconsin Package™ from Accelrys, Inc., San Diego, Calif.

The CLUSTAL program is well described by Higgins and Sharp, *Gene* 73: 237-244 (1988); Higgins and Sharp, CABIOS 5: 151-153 (1989); Corpet, et al., Nucleic Acids Research 16: 10881-90 (1988); Huang, et al., Computer Applications in the *Biosciences* 8: 155-65 (1992), and Pearson, et al., Methods in Molecular Biology 24: 307-331 (1994). A description of BLAST (Basic Local Alignment Search Tool) is provided by Altschul, S. F., et al., (1993) J. Mol. Biol. 215:403-410.

Identity to the sequence of the present invention would mean a polynucleotide sequence having at least 85% sequence identity, wherein the percent sequence identity is based on the entire length of SEQ ID NO: 1 or SEQ ID NO: 3.

Variants of the nucleotide sequences disclosed herein are also encompassed by the present invention. By "variants" is intended substantially similar sequences wherein one or more bases have been modified, removed or added. For nucleotide sequences, naturally-occurring variants can be identified with the use of well-known molecular biology techniques, as, for example, with polymerase chain reaction (PCR) and hybridization techniques as outlined above. Variant nucleotide sequences also include synthetically-derived nucleotide sequences, such as those generated, for example, by using site-directed mutagenesis. Generally, variants of a particular nucleotide sequence of the invention will have at least about 75%, 80%, 85%, 86%, 87%, 88%, 89%, 90%, 91%, 92%, 93%, 94%, 95%, 96%, 97%, 98%, 99% or more sequence identity to that particular nucleotide sequence as determined by sequence alignment programs described elsewhere herein, using default parameters.

The AP2 domain is highly conserved among CBF genes, and some species share an additional conserved region bracketing the AP2 domains. (Jaglo et al., Plant Phys. 127:910-917, 2001). Thus one of skill in the art would recognize that variants most likely to retain function are those in which the AP2 domain is undisturbed. Surprisingly, however, the current application provides a novel sequence in which the AP2 domain is altered. FIG. 1 provides a multiple sequence alignment of several CBF polypeptides.

The expression cassette may also include, at the 3' terminus of the heterologous nucleotide sequence of interest, a transcriptional and translational termination region functional in plants. The termination region can be native with the promoter nucleotide sequence present in the expression cassette, can be native with the DNA sequence of interest, or can be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Nat. Acad. Sci.* USA 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA*, pages 237-256; and maize chlorotic mottle virus leader (MCMV) Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments can be manipulated so as to provide for the DNA sequences in the proper orientation and, as appropriate, in the proper reading frame. Toward this end, adapters or linkers can be employed to join the DNA fragments, or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing the claimed sequences under the control of an operably linked promoter. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector, comprising a sequence of the present invention operably linked to a promoter in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At a minimum, between these border sequences is the gene to be expressed under control of an operably-linked promoter. In preferred embodiments, a selectable marker and a reporter gene are also included.

For ease of obtaining sufficient quantities of vector, a bacterial origin that allows replication in *E. coli* is preferred.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419423; glyphosate, Shaw et al. (1986) *Science* 233:478-481; phosphinothricin, DeBlock et al. (1987) *EMBO J.* 6:2513-2518.

Other genes that could serve utility in the recovery of transgenic events but might not be required in the final product would include, but are not limited to, examples such as GUS (β-glucuronidase), Jefferson (1987) *Plant Mol. Biol. Rep.* 5:387); GFP (green fluorescence protein), Chalfie et al. (1994) *Science* 263:802, and Gerdes (1996) *FEBS Lett.* 389:44-47; DSred (Dietrich et al. (2002) Biotechniques 2(2):286-293); luciferase, Teeri et al. (1989) *EMBO J.* 8:343; KN1 (Smith et al. (1995) Dev. Genetics 16(4):344-348); Sugary1, Rahman et al. (1998) Plant Physiol. 117: 425-435; James et al. (1995) Plant Cell 7:417-429 and GenBank Accession U18908; and systems utilizing the maize genes encoding enzymes for anthocyanin production, including CRC, P (Bruce et al. (2000) Plant Cell 12(1):65-79, and R (Ludwig et al. (1990) *Science* 247:449).

The transformation vector comprising an isolated polynucleotide of the present invention, operably linked to a promoter sequence in an expression cassette, can be used to transform any plant. In this manner, genetically modified plants, plant cells, plant tissue, seed, and the like can be obtained. Transformation protocols can vary depending on the type of plant or plant cell targeted for transformation, e.g., monocot or dicot. Suitable methods of transforming plant cells include microinjection, Crossway et al. (1986) *Biotechniques* 4:320-334; electroporation, Riggs et al. (1986) *Proc. Natl. Acad. Sci. USA* 83:5602-5606; *Agrobacterium*-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945,050; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature* (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. G. P. Chapman et al. (Longman, N.Y.), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed can be grown into plants in accordance with conventional ways. See, for example, McCormick et al. (1986) *Plant Cell Reports* 5:81-84. These plants can then be pollinated with the same transformed strain or different strains. The resulting plants having expression of the desired characteristic can then be identified. Two or more generations can be grown to ensure that the desired phenotypic characteristic is stably maintained and inherited under conditions of interest.

In certain embodiments the nucleic acid sequences of the present invention can be used in combination ("stacked") with other polynucleotide sequences of interest in order to create plants with a desired phenotype. The polynucleotides of the present invention may be stacked with any gene or combination of genes, and the combinations generated can include multiple copies of any one or more of the polynucleotides of interest. The desired combination may affect one or more traits; that is, certain combinations may be created for modulation of gene expression involved in plant response to stress. Other combinations may be designed to produce plants with a variety of desired traits, including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737, 514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method, including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or overexpression cassettes to generate the desired combination of traits in the plant.

The transformed plants of the invention may be used in a plant breeding program. The goal of plant breeding is to combine, in a single variety or hybrid, various desirable traits. For field crops, these traits may include, for example, resistance to diseases and insects, tolerance to heat, cold, and/or drought, reduced time to crop maturity, greater yield, and better agronomic quality. With mechanical harvesting of many crops, uniformity of plant characteristics such as germination and stand establishment, growth rate, maturity, and plant and ear height, is desirable. Traditional plant breeding is an important tool in developing new and improved commercial crops. This invention encompasses methods for producing a maize plant by crossing a first parent maize plant with a second parent maize plant wherein one or both of the parent maize plants is a transformed plant, as described herein.

Plant breeding techniques known in the art and used in a maize plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular maize plant using transformation techniques, could be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant. As used herein, "crossing" can refer to a simple X by Y cross, or the process of backcrossing, depending on the context.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process in maize, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

The following examples are offered by way of illustration and not by way of limitation.

EXAMPLES

Example 1

Expression of Transgenes in Monocot Cells

A plasmid vector is constructed comprising the full-length polynucleotide of SEQ ID NO: 1 or SEQ ID NO: 3, operably linked to a heterologous promoter, such as a stress-responsive promoter, for example rab17, rd29A, rip2, or mlip15. This construct can then be introduced into maize cells by the following procedure.

Immature maize embryos are dissected from developing caryopses. The embryos are isolated 10 to 11 days after pollination when they are 1.0 to 1.5 mm long. The embryos are then placed with the axis-side facing down and in contact with agarose-solidified N6 medium (Chu et al. (1975) *Sci.*

*Sin. Peking* 18:659-668). The embryos are kept in the dark at 27° C. Friable embryogenic callus, consisting of undifferentiated masses of cells with somatic proembryoids and embryoids borne on suspensor structures, proliferates from the scutellum of these immature embryos. The embryogenic callus isolated from the primary explant can be cultured on N6 medium and sub-cultured on this medium every 2 to 3 weeks.

The plasmid p35S/Ac (Hoechst Ag, Frankfurt, Germany) or equivalent may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNA are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton flying disc (Bio-Rad Labs). The particles are then accelerated into the corn tissue with a Biolistic PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of actively growing callus about 1 cm in diameter can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 2

Expression of Transgenes in Dicot Cells

Soybean embryos are bombarded with a plasmid comprising a CBF polynucleotide operably linked to a promoter, as follows. To induce somatic embryos, cotyledons of 3-5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the sequence of interest operably linked to a promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl CaCl$_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 3

Identification of the Gene from a Computer Homology Search

Gene identities can be determined by conducting BLAST (Basic Local Alignment Search Tool; Altschul, S. F., et al., (1993) J. Mol. Biol. 215:403-410; see also information available from NCBI (National Center for Biotechnology Information, U.S. National Library of Medicine, 8600 Rockville Pike, Bethesda, Md. 20894)) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN program. The DNA sequences are translated in all reading frames and compared for similarity to all publicly available protein sequences contained in the "nr" database using the BLASTX program (Gish, W. and States, D. J. *Nature Genetics* 3:266-272 (1993)) provided by the NCBI. In some cases, the sequencing data from two or more clones containing overlapping segments of DNA are used to construct contiguous DNA sequences.

Sequence alignments and percent identity calculations can be performed using software such as GAP, BestFit, PileUp or Pretty, available as part of the GCG® Wisconsin Package™ from Accelrys, Inc., San Diego, Calif. Default parameters for pairwise alignments of polynucleotide sequences using GAP and BestFit are Gap Creation Penalty=50, Gap Extension Penalty=3; nwsgapdna.cmp is the scoring matrix. Default parameters for pairwise alignments for polypeptide sequences using GAP and BestFit are Gap Creation Penalty=8, Gap Extension Penalty=2; BLOSUM62 is the scoring matrix. There is no penalty for gaps at ends of polynucleotide or polypeptide alignments.

Default parameters for polynucleotide sequence comparison using PileUp and Pretty are: Gap Creation Penalty=5, Gap Extension Penalty=1. Default parameters for polypeptide sequence comparison using PileUp or Pretty are Gap Creation Penalty=8, Gap Extension Penalty=2; BLOSUM62 is the scoring matrix.

Sequence alignments can also be accomplished with the Megalign program of the LASERGENE bioinformatics computing suite (DNASTAR Inc., Madison, Wis.). Multiple alignment of the sequences can be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

Other pairwise comparison tools are also available and known to those of skill in the art.

Example 4

Time Course of Cold-Induced Gene Expression in B73 Seedling Shoots

Seeds of maize inbred B73 were germinated and grown in the greenhouse under optimal temperatures of approximately 28° C. during the day and 25° C. during the night. After ten days of growth they were moved into growth chambers set at a constant chilling temperature of 10° C. under 16-hour (h) day lengths. Seedling shoots were harvested at various time points after exposure to the chilling temperature, starting at 0h (which served as control) and continuing at 0.5 h, 1 h, 4 h, 8 h and 24 h. At the end of the 24 h period of cold exposure, seedlings were allowed to recover at optimal temperatures of 25° C./22° C. (16 h day/8 h night) and were harvested after 48 hours to constitute the treatment '48 h Rec' (48 hours of recovery).

At harvest, seedling tissues above the coleoptile, comprising leaves and stems, were ground in liquid nitrogen and stored at −80° C. before submission for RNA extraction and Agilent profiling using the Agilent Oligo Microarray Kit (Protocol Version 5.0, June 2003) and the Agilent Fluorescent Linear Amplification Kit (Protocol Version 3.0, June 2002) (both, Agilent Technologies, Palo Alto, Calif.). RNA expression levels at each time point were compared against the control (zero time-point). Thus, expression ratios were obtained for 0.5 h, 1 h, 4 h, 8 h and 24 h of cold treatment and 48 h of recovery. Results are shown in Table 1.

The time course of cold-induced gene expression provided an understanding of genes expressed early upon stress exposure, those that are expressed later during stress exposure, and those that express after the stress has been relieved and the plant has been allowed to recover. A CBF-like gene (SEQ ID NO: 1-2) showed its second highest expression level at the earliest measured time point (0.5 h relative to zero time), and its highest expression level at 1 hour from the start time. This shows a very early induction pattern of CBF upon exposure to stress. This is in accordance with published reports on the time-course of CBF induction. It is also consistent with the role of CBF acting as a transcription factor to induce the simultaneous expression of several stress-responsive genes.

TABLE 1

| Expression of ZmCBF2 with exposure to chilling | |
|---|---|
| Time | Relative to zero level at start |
| 0.5 h | 3.42 |
| 1 h | 4.46 |
| 4 h | 3.3 |
| 8 h | −1.49 |
| 24 h | −2.5 |
| 48 h Rec | −17.77 |

Example 5

Transient Activity Assay for CBF

A transient assay was designed to check for CBF activity using the expression of the maize CRC gene from the RAB17 promoter as a reporter for CBF activity. The objective was to identify a CBF protein with the best activity which would then be expressed in transgenic plants under the stringent control of a stress-inducible promoter. This would allow the high activity of CBF to be prevalent only during times of stress, thus preventing any pleiotropic effects from the highly active transcription factor.

The RAB17 promoter comprises CRT/DRE elements to which CBF binds (see SEQ ID NO: 5). Consequently, re-transformation of transgenic embryos already comprising the RAB17::CRC construct, with a CBF construct, should allow activation of RAB17 in the first construct. This activation will produce reporter gene (CRC) expression, which can be visualized through red/purple anthocyanin pigmentation in cultured embryos or callus tissue.

Maize plants, hemizygous for a single-copy Rab17::CRC event previously confirmed as showing CRC expression upon induction by drought or ABA treatment, were pollinated with inbred GS3, which enhances transformation with Agrobacterium. The resulting embryos segregated in a 1:1 ratio of transgenic:non-transgenic embryos. Immature embryos were isolated 9 to 10 days after pollination (DAP) and cultured with Agrobacterium suspension comprising a CBF construct of interest, following the standard Agrobacterium transformation protocol as provided in Example 8.

After infection with Agrobacterium suspension, the embryos were incubated at 20° C. for 3 days and then moved to a 26° C. culture room for continuous culture. CRC expression was monitored at 7-8 days after infection, and the final score (counts of CRC-expressing embryos) for CRC expression was determined 10-11 days after infection.

ZmCBF1 (SEQ ID NO: 3-4), ZmCBF2 (SEQ ID NO: 1-2) and RyeCBF31 (SEQ ID NO: 10) were tested in this transient expression system. Each CBF gene was operably linked to the ubiquitin promoter. Certain constructs further comprised the C1 activation domain (C1 AD) from maize (Goff et al. (1991) Genes Dev. 5:298-309; Singer et al. (1998) Genet. Res. 71(2):127-132), fused to either the N or C terminus of each CBF gene.

Results are shown in Table 2 for the ZmCBF2 and RyeCBF31 proteins in combination with the C1 activation domain. The activation percent represents the % of embryos displaying CRC, with 50% being the expected maximum in the segregating population.

TABLE 2

| Promoter | Coding Region | Activation (%) |
|----------|---------------|----------------|
| Ubiquitin | C1 AD + Rye-CBF31 | 9.1 |
| Ubiquitin | C1 AD + Zm-CBF2 | 26.4 |
| Ubiquitin | Rye-CBF31 + Cq AD | 19.5 |
| Ubiquitin | Zm-CBF2 + C1 AD | 35.2 |

In this assay system, ZmCBF2 produces a higher activation % than Rye CBF31. Further, the fusion of the C1 activation domain at the C-terminus of CBF produces higher activity levels than does fusion of the C1 activation domain at the N-terminus.

Example 6

Transient Activity Assay for CBF Under Cold Stress

The transient assay system of Example 5 was also used to test ZmCBF1 (SEQ ID NO: 3) and RyeCBF31 (SEQ ID NO: 10) in constructs comprising the mlip15 promoter (SEQ ID NO: 9).

After infection with Agrobacterium suspension, the embryos were incubated at 20° C. For cold treatment to induce ZmLIP15, 25 to 30 infected embryos were transferred to a fresh plate at 4 to 5 days after infection. These were kept at 4° C. for 4 hours, and then returned to 26° C. for monitoring CRC activity as in Example 5.

Results are shown in Table 3.

TABLE 3

| Promoter | Coding Region | Activation (%) | Treatment |
|----------|---------------|----------------|-----------|
| Ubiquitin | Zm-CBF1 | 51.8 | None |
| Zm-Cyclo1 | GUS | 0.0 | None |
| Zm-LIP15 | Zm-CBF1 | 0.0 | None |
| Zm-LIP15 | Zm-CBF1 | 23.3 | Cold |
| Zm-LIP15 | Zm-CBF2 | 0.0 | None |
| Zm-LIP15 | Zm-CBF2 | 37.0 | Cold |

The construct containing ZmCBF1, without a C1 activation domain fusion, and expressed from the ubiquitin promoter, produced the fastest and strongest CRC expression in transient assays. This expression is relative to other constructs that either contained a C1 activation domain fusion or were linked to stress-inducible promoters. Constructs containing ZmCBF2 and Rye CBF31 expressed from the ubiquitin promoter are awaiting test in the transient assay system.

Example 7

Activity of CBF on Reporter Gene Expression in Stable Transformants

Transgenic plants containing ZmCBF1, ZmCBF2 or Rye CBF31, expressed from constitutive or stress-inducible promoters, are crossed with plants containing the reporter construct RAB17::CRC to create progeny that will show stable expression of the reporter gene resulting from the activity of CBF on the RAB17 promoter.

Transgenic maize plants comprising Rab17::CRC, a construct previously confirmed to show CRC expression upon induction by drought or ABA treatment, are crossed with transgenic plants comprising a Rab17::ZmCBF2 construct, such as proprietary Pioneer plasmid PHP22621, or other construct comprising a CBF coding sequence operably linked to a constitutive promoter, such as ubiquitin, or a stress-inducible promoter, such as rd29A, rip2 or mlip15. The construct further comprises LTP2::DS-RED2 (Kalla et al., Plant J (1994) 6:849-860; Dietrich et al. (2002) Biotechniques 2(2):286-293) which allows visualization of segregation among kernels on the ear. Red-fluorescing kernels are selected and planted. Progeny are evaluated for expression of the reporter gene as well as tolerance to cold or drought stress.

Example 8

Standard Agro Transformation Protocol as Referred to in Example 5

For Agrobacterium-mediated transformation of maize, the method of Zhao is employed (U.S. Pat. No. 5,981,840, and PCT patent publication WO98/32326, the contents of which are hereby incorporated by reference). Briefly, immature embryos are isolated from maize and the embryos immersed in an Agrobacterium suspension, where the bacteria are capable of transferring the gene of interest to at least one cell of at least one of the immature embryos (step 1: the infection step). The embryos are then co-cultured for a time with the Agrobacterium on solid medium (step 2: the co-cultivation step). During the co-cultivation step infected embryos are cultured at 20° C. for 3 days, and then at 26° C. for 4 days. Following this co-cultivation period an optional "resting" step is contemplated in which the embryos are incubated in the presence of at least one antibiotic known to inhibit the growth of *Agrobacterium*, without the addition of a selective agent for plant transformants (step 3: resting step). Transient expression based on a color marker can be monitored during the co-cultivation and the resting steps. Next, inoculated embryos are cultured on medium containing a selective agent and growing transformed callus is recovered (step 4: the selection step). Finally, calli grown on selective medium are cultured on solid medium to regenerate transformed plants (step 5: the regeneration step).

Example 9

Native Expression of ZmCBF1 in B73 Seedlings

Seeds of maize inbred B73 were germinated and grown in the greenhouse under optimal temperatures of approximately 28° C. during the day and 25° C. during the night. After ten days of growth they were moved into growth chambers set at a constant chilling temperature of 10° C. under 16-hour (h) day lengths. Seedling shoots from the V1 stage were harvested at various time points after exposure to the chilling temperature, starting at 0 h (which served as control) and continuing at 0.25 h, 1 h, 4 h, 8 h and 24 h. At the end of the 24 h period of cold exposure, seedlings were allowed to recover at optimal temperatures of 23° C. (16 h day/8 h night) and were harvested after 48 hours under the optimal temperature to constitute the treatment '48 h Rec' (48 hours of recovery).

At harvest, seedling tissues above the coleoptile, comprising leaves and stems, were ground in liquid nitrogen and stored at −80° C. before RNA extraction and RT-PCR using gene-specific primers for ZmCBF1 (SEQ ID NO: 3) over a 35-cycle period. Expression of ZmCBF was not detectable at the zero point or at 0.25 hours. Expression was detected after 1 hour of cold treatment, peaking at 4 hours of cold treatment. Expression at the 8 h and 24 h points was less than the level indicated at 1 h. Expression was not detected at the 48-hour recovery point. This is in accordance with published reports on the time-course of CBF induction. It is also consistent with the role of CBF acting as a transcription factor to induce the simultaneous expression of several stress-responsive genes.

Example 10

Chilling Tolerance Exhibited by ZmCBF1 in Maize Seedlings

As described in Example 1, maize was transformed with a construct comprising a maize, *Arabidopsis*, or rye CBF coding region, driven by a constitutive (ubiquitin) or stress-inducible promoter, such as rab17, rd29a, mlip15, or the native promoter of a CBF gene. Certain constructs further comprised the C1 activation domain (Goff et al. (1991) Genes Dev. 5:298-309; Singer et al. (1998) Genet. Res. 71(2):127-132) or the OP2 activation domain (Schmitz et al. (1997) Nucleic Acids Res. 25(4):756-763), fused to either the N or C terminus of the CBF coding region.

Regenerated plants were backcrossed with pollen from recurrent parent, and the resulting T2 seeds were planted and grown to V1-V2 (10 days from sowing) at optimal growth conditions of 28° C.-26° C. day-night temperatures in a 16 h-8 h day-night regime. A total of 18 seeds were planted with an expectation of observing 9 transgene-positive plants and 9 transgene-negative plants.

Ten-day-old seedlings were leaf-painted with 1% Liberty® (a.i., glufosinate) to determine transgenic positive and negative plants, and were marked as such based on the leaf-painting results. At 14 days after sowing, they were subjected to a low-temperature stress of 13° C.-7° C. day-night temperatures for the next 14 days. At the end of the 14-day stress period, plants were cut at the base and whole-shoot fresh weight was determined.

For five constructs shown in Table 4, PHP17421, PHP18990, PHP18991, PHP18992 and PHP19021, transgenic plants within several events showed increased growth under low-temperature stress, relative to their non-transgenic sib plants. As an example, fresh weight data for PHP18990 seedlings are provided in FIG. 3.

TABLE 4

| PHP # | Promoter | Coding Region |
| --- | --- | --- |
| 17421 | Ubiquitin | Zm-CBF1 |
| 18990 | Rd29a | ZmCBF1 |
| 18991 | Rd29a | ScCBF31 |
| 18992 | Mlip15 | ZmCBF1 |
| 19021 | Mlip15 | ScCBF31 |

Example 11

Freezing Tolerance in Maize Seedlings Overexpressing ZmCBF1

As described in Example 1, maize was transformed with a construct comprising the ubiquitin promoter driving ZmCBF1. Regenerated plants were backcrossed with pollen from recurrent parent, and the resulting T2 seeds were planted in 4" pots, using 3 seeds/pot (18 seeds/event) and allowed to grow at optimal growth conditions in the greenhouse. After plants had reached the V1-V2 stage (10 days after planting), leaves were painted with 1.0% Liberty® (a.i., glufosinate), to screen for the presence or absence of the transgene. After 4 days, when visible leaf scorching could be observed as a result of the herbicide application, individual plants were scored as either transgene positive or negative.

The flats containing the pots with the 14-day-old seedlings were moved to growth chambers where the temperature was lowered to 4° C. overnight to allow complete chilling of the potting medium. Thereafter, the temperature was lowered to −4° C. and retained for 3 hours. At the end of the freezing period, plants were allowed to recover at 4° C. overnight, and then moved to the optimal temperature conditions of the greenhouse. The plants were scored for survival 3-4 days after the freezing treatment.

Screening of 19 events of the UBI::ZmCBF1 construct revealed three events that were freezing tolerant. Results are shown in Table 5.

TABLE 5

| Event number | No. of survivors/ total no. of transgenic positives | % survival | No. of survivors/ total no. of transgenic negatives | % survival |
|---|---|---|---|---|
| 8 | 8/11 | 73 | 0/7 | 0 |
| 16 | 5/8 | 63 | 0/10 | 0 |
| 23 | 6/11 | 55 | 0/7 | 0 |

Example 12

Evaluation of Rd29a::RyeCBF31 Transgenic Plants for Photosynthetic Performance

Maize plants transgenic (hybrid material which contained three doses of the recurrent parent that was crossed to elite inbred, and then selfed) for a construct comprising rd29a::ryeCBF31 were subjected to drought stress at different points during the growth period, i.e. at 2, 5, 8, 10 and 12 weeks after sowing. Water was withheld at these specified time points and plants were monitored for photosynthesis from the time of withholding water until photosynthesis was reduced to zero. Photosynthesis measurements were recorded using a LI-COR 6400 (LI-COR, Lincoln, Nebr.) portable photosynthesis machine connected to a fluorescence chamber. Standard protocols specified by the manufacturer were used to record photosynthesis and chlorophyll fluorescence simultaneously. At the point when photosynthesis was lowered to zero, re-watering was initiated.

Results are shown in FIG. 2. The photosynthesis readings are the average of three transgenic plants and three non-transgenic plants, where the stress was imposed at 8 weeks after sowing and 10 weeks after sowing. Transgenic plants are indicated by 'tng' and non-transgenic plants or wild-type are indicated by 'wt'.

Example 13

Overexpression of ZmCBF1 in *Arabidopsis* (Construct PHP 17421-UBI::ZmCBF1 or PHP18990-RD29A::ZmCBF1)

Transgenic *Arabidopsis thaliana* (Ecotype Columbia) seeds heterozygous for the CBF construct PHP17421 (UBI::ZmCBF1) or PHP18990 (RD29A::ZmCBF1) were germinated on medium comprising 0.5×MS salts (Murashige and Skoog (1962) Physiol. Plant. 15:473) with no sucrose, and seedlings were grown for 20 days. The plates were then subjected to a freezing temperature of −7° C. for 4 hours and thereafter allowed to recover at room temperature (22° C.) for 3 to 4 days. The number of surviving plants was counted after the recovery period.

Eight of twelve events of the construct expressing ZmCBF1 from the stress-inducible *Arabidopsis* promoter, RD29A, showed improved freezing tolerance over the wild-type. Results are shown in Table 6.

TABLE 6

| Construct | Event | Total no. of plants | No. of Survivors | % Survival |
|---|---|---|---|---|
| 18990 | 1 | 10 | 8 | 80% |
| 18990 | 2 | 9 | 4 | 44% |
| 18990 | 3 | 12 | 9 | 75% |
| 18990 | 4 | 10 | 5 | 50% |
| 18990 | 5 | 9 | 4 | 44% |
| 18990 | 6 | 11 | 2 | 18% |
| 18990 | 7 | 11 | 1 | 9% |
| 18990 | 8 | 18 | 1 | 6% |
| 18990 | 9 | 19 | 2 | 11% |
| 18990 | 10 | 14 | 11 | 79% |
| 18990 | 11 | 13 | 12 | 92% |
| 18990 | 12 | 20 | 16 | 80% |
| 18990 | WT1 | 13 | 2 | 15% |
| 18990 | WT2 | 17 | 6 | 35% |
| 18990 | WT3 | 10 | 1 | 10% |
| 18990 | WT4 | 19 | 3 | 16% |

The construct expressing ZmCBF1 from the UBI promoter showed 5 events out of a total of 12 that had improved freezing tolerance relative to the wildtype.

Transgenic *Arabidopsis thaliana* (Ecotype Columbia) heterozygous for the CBF construct PHP17421 (UBI::ZmCBF1) was also evaluated for tolerance to drought stress. Pots were filled with Metro-Mix 200 with 90 g of Osmocote® controlled release fertilizer (18-6-12) per 2.8 cu ft bag of soil. At planting the potting medium was watered to saturation with water plus 20-10-20 fertilizer and allowed to drain. *Arabidopsis* seeds were sown at nine seeds per pot, and allowed to germinate and grow under 17-hour day length at a temperature of 22° C. during the day, 20° C. during the night, under light intensities of ~200 uE. During the first two weeks, watering was done without added fertilizers. At two weeks water was withheld. Effect of the stress was evident as the plants entered the reproductive phase. The trend towards complete wilting was monitored by digital imaging. In one of twelve events tested, wildtype plants were completely wilted at 36 days after stress, while transgenic plants survived. This event was then subjected to a second test and the drought tolerance effect was confirmed.

Example 14

Constitutive Expression of ZmCBF1 in Maize

Constitutive expression of ZmCBF1 from the UBI promoter in construct PHP17421 caused severe reduction in plant height of transgenic events, as observed by visual observation throughout the entire growth cycle. We overcame this pleiotropic effect by using stress-inducible promoters including RD29A and RAB17.

Example 15

Expression Analysis of Transgenic Maize Expressing UBI::ZmCBF1

Seedling shoots of transgenic maize plants (V4) expressing UBI::ZmCBF1, event number 7, were harvested, ground in liquid nitrogen and extracted for mRNA. Using the Agilent chip system (see Example 4), the RNA expression in the transgenic plants was compared with that of non-transgenic plants. Several genes were found to be upregulated in the transgenic plants relative to the control, with a major proportion of these being unknown genes. From amongst the upregulated genes, a list of all public maize genes with known or putative function that showed upregulation above the two-fold limit was compiled. To this list was added a small selection of maize homologs of known genes from other species that were known to be stress-regulated. Thus a total list of 66 is presented in the table (FIG. 4) as those that were upregulated above the two-fold level. Of these, 57 are known maize genes, while 9 are maize homologs of known stress-responsive genes in other species, primarily, rice. In Arabidopsis, homologs of several of these 66 are known to be either stress-responsive or part of the CBF regulon (Seki et al. 2001. Plant Cell 13: 61-72; Zhang et al., 2004. Plant J 39: 905-919).

The above examples are provided to illustrate the invention but not to limit its scope. Other variants of the invention will be readily apparent to one of ordinary skill in the art and are encompassed by the appended claims.

All publications and patent applications cited in the specification are indicative of the level of skill of those in the art to which this invention pertains. All publications, patents, patent applications, and computer programs cited herein are incorporated by reference to the same extent as if specifically and individually indicated to be incorporated by reference.

That which is claimed is:

1. A method for increasing plant tolerance to abiotic stress due to low temperature or dehydration, comprising the steps of:
   (a) transforming a plant with a transformation vector comprising an isolated polynucleotide encoding a transcription factor of SEQ ID NO: 4; and
   (b) expressing said polynucleotide encoding said transcription factor, wherein said expression results in increased tolerance to low temperature or dehydration stress relative to that of said plant prior to transformation.

2. The method of claim 1, wherein said polynucleotide is operably linked to a promoter which drives expression in a stress-responsive or tissue-preferred manner.

* * * * *

SEQUENCE LISTING

```
<160> NUMBER OF SEQ ID NOS: 12

<210> SEQ ID NO 1
<211> LENGTH: 696
<212> TYPE: DNA
<213> ORGANISM: Zea mays
<220> FEATURE:
<221> NAME/KEY: CDS
<222> LOCATION: (1)...(693)
<223> OTHER INFORMATION: ZmCBF2
<220> FEATURE:
<221> NAME/KEY: misc_feature
<222> LOCATION: (106)...(147)
<223> OTHER INFORMATION: CBF-specific domain
<220> FEATURE:
<221> NAME/KEY: misc_feature
<222> LOCATION: (154)...(342)
<223> OTHER INFORMATION: AP2 domain

<400> SEQUENCE: 1 atg tgc cca acc aag aag ggg atg acc gga gag ccg agc tcg cca tgc      48
Met Cys Pro Thr Lys Lys Gly Met Thr Gly Glu Pro Ser Ser Pro Cys
 1               5                  10                  15 agc tcg gca tca gcc tcg acc tta ccg gag cac cac cag acg gtg tgg      96
Ser Ser Ala Ser Ala Ser Thr Leu Pro Glu His His Gln Thr Val Trp
             20                  25                  30 acg tcg ccg ccg aag cgg cca gcg ggg cgg acc aag ttc cgg gag acg     144
Thr Ser Pro Pro Lys Arg Pro Ala Gly Arg Thr Lys Phe Arg Glu Thr
         35                  40                  45 cgg cac ccg gtg ttc cgc ggc gtc cgg cgc cgg ggc agc gcc ggg cgg     192
Arg His Pro Val Phe Arg Gly Val Arg Arg Arg Gly Ser Ala Gly Arg
     50                  55                  60 tgg gtg tgc gag gtg cgc gtg ccg ggg agg cgc ggc tgc agg ctc tgg     240
Trp Val Cys Glu Val Arg Val Pro Gly Arg Arg Gly Cys Arg Leu Trp
 65                  70                  75                  80 ctc ggc acc ttc gac acg gcc gag gcg gcg gcc cgc gcg cac gac gcc     288
Leu Gly Thr Phe Asp Thr Ala Glu Ala Ala Ala Arg Ala His Asp Ala
                 85                  90                  95 gcc atg ctc gcc ctc gcc ggc gcg ggc gcc tgc tgc ctc aac ttc gcc     336
Ala Met Leu Ala Leu Ala Gly Ala Gly Ala Cys Cys Leu Asn Phe Ala
            100                 105                 110 gac tcg gcc tgg ctc ctc gcg gtc ccg gcc tcg tgc gcc agc ctc gcc     384
Asp Ser Ala Trp Leu Leu Ala Val Pro Ala Ser Cys Ala Ser Leu Ala
        115                 120                 125 gag gtc cgc cac gcg gtc gcg gac gcc gtg gag gac ttc ctc cgc cat     432
Glu Val Arg His Ala Val Ala Asp Ala Val Glu Asp Phe Leu Arg His
    130                 135                 140 cag gtg gtc ccg gag gac gac gcc ctc gcg gcc acg ccg tcg tcg cct     480
Gln Val Val Pro Glu Asp Asp Ala Leu Ala Ala Thr Pro Ser Ser Pro
145                 150                 155                 160
```

-continued

| | | |
|---|---|---|
| tcc agc gaa gac ggc agc acc tct gat ggc ggg gag tcc tcc tct gat<br>Ser Ser Glu Asp Gly Ser Thr Ser Asp Gly Gly Glu Ser Ser Ser Asp<br>                    165                      170                      175 | 528 |
| tcc tct ccg ccc acc ggg gcc tcg ccg ttc gaa ttg gat gtg ttc aac<br>Ser Ser Pro Pro Thr Gly Ala Ser Pro Phe Glu Leu Asp Val Phe Asn<br>        180                      185                      190 | 576 |
| gac atg agc tgg gac ctg cac tac gcg agc ttg gcg cag gga ttg ctc<br>Asp Met Ser Trp Asp Leu His Tyr Ala Ser Leu Ala Gln Gly Leu Leu<br>            195                      200                      205 | 624 |
| gtg gag cca ccg tcc gcg gtc acg gcg ctc atg gac gaa ggc ttc gcc<br>Val Glu Pro Pro Ser Ala Val Thr Ala Leu Met Asp Glu Gly Phe Ala<br>210                      215                      220 | 672 |
| gat gtg ccg ctc tgg agc tac tag<br>Asp Val Pro Leu Trp Ser Tyr<br>225                      230 | 696 |

<210> SEQ ID NO 2
<211> LENGTH: 231
<212> TYPE: PRT
<213> ORGANISM: Zea mays

<400> SEQUENCE: 2

Met Cys Pro Thr Lys Lys Gly Met Thr Gly Glu Pro Ser Ser Pro Cys
  1               5                  10                  15

Ser Ser Ala Ser Ala Ser Thr Leu Pro Glu His His Gln Thr Val Trp
             20                  25                  30

Thr Ser Pro Pro Lys Arg Pro Ala Gly Arg Thr Lys Phe Arg Glu Thr
         35                  40                  45

Arg His Pro Val Phe Arg Gly Val Arg Arg Gly Ser Ala Gly Arg
     50                  55                  60

Trp Val Cys Glu Val Arg Val Pro Gly Arg Arg Gly Cys Arg Leu Trp
 65                  70                  75                  80

Leu Gly Thr Phe Asp Thr Ala Glu Ala Ala Arg Ala His Asp Ala
                 85                  90                  95

Ala Met Leu Ala Leu Ala Gly Ala Gly Ala Cys Cys Leu Asn Phe Ala
            100                 105                 110

Asp Ser Ala Trp Leu Leu Ala Val Pro Ala Ser Cys Ala Ser Leu Ala
        115                 120                 125

Glu Val Arg His Ala Val Ala Asp Ala Val Glu Asp Phe Leu Arg His
    130                 135                 140

Gln Val Val Pro Glu Asp Ala Leu Ala Ala Thr Pro Ser Ser Pro
145                 150                 155                 160

Ser Ser Glu Asp Gly Ser Thr Ser Asp Gly Gly Glu Ser Ser Ser Asp
                165                 170                 175

Ser Ser Pro Pro Thr Gly Ala Ser Pro Phe Glu Leu Asp Val Phe Asn
            180                 185                 190

Asp Met Ser Trp Asp Leu His Tyr Ala Ser Leu Ala Gln Gly Leu Leu
        195                 200                 205

Val Glu Pro Pro Ser Ala Val Thr Ala Leu Met Asp Glu Gly Phe Ala
    210                 215                 220

Asp Val Pro Leu Trp Ser Tyr
225                 230

<210> SEQ ID NO 3
<211> LENGTH: 699
<212> TYPE: DNA
<213> ORGANISM: Zea mays
<220> FEATURE:

```
<221> NAME/KEY: CDS
<222> LOCATION: (1)...(696)
<223> OTHER INFORMATION: ZmCBF1
<220> FEATURE:
<221> NAME/KEY: misc_feature
<222> LOCATION: (124)...(165)
<223> OTHER INFORMATION: CBF-specific domain
<220> FEATURE:
<221> NAME/KEY: misc_feature
<222> LOCATION: (172)...(354)
<223> OTHER INFORMATION: AP2 domain

<400> SEQUENCE: 3
```

| | | | | | | | | | | | | | | | | |
|---|---|---|---|---|---|---|---|---|---|---|---|---|---|---|---|---|
| atg | gag | tac | gcc | gcc | gtc | ggc | tac | ggc | tac | ggg | tac | ggg | tac | gac | gag | 48 |
| Met | Glu | Tyr | Ala | Ala | Val | Gly | Tyr | Gly | Tyr | Gly | Tyr | Gly | Tyr | Asp | Glu | |
| 1 | | | | 5 | | | | | 10 | | | | | 15 | | |
| cgc | cag | gag | ccg | gcg | gag | tcc | gcg | gac | ggc | ggc | ggc | ggc | ggc | gac | gac | 96 |
| Arg | Gln | Glu | Pro | Ala | Glu | Ser | Ala | Asp | Gly | Gly | Gly | Gly | Gly | Asp | Asp | |
| | | | 20 | | | | | 25 | | | | | 30 | | | |
| gag | tac | gcg | acg | gtg | ctg | tcg | gcg | cca | ccc | aag | cgg | ccg | gcg | ggg | cgg | 144 |
| Glu | Tyr | Ala | Thr | Val | Leu | Ser | Ala | Pro | Pro | Lys | Arg | Pro | Ala | Gly | Arg | |
| | | 35 | | | | | 40 | | | | | 45 | | | | |
| acc | aag | ttc | cgg | gag | acg | cgg | cac | ccc | gtg | tac | cgc | ggc | gtg | cgg | cgg | 192 |
| Thr | Lys | Phe | Arg | Glu | Thr | Arg | His | Pro | Val | Tyr | Arg | Gly | Val | Arg | Arg | |
| 50 | | | | | 55 | | | | | 60 | | | | | | |
| cgc | ggg | ccc | gcg | ggg | cgc | tgg | gtg | tgc | gag | gtc | cgc | gag | ccc | aac | aag | 240 |
| Arg | Gly | Pro | Ala | Gly | Arg | Trp | Val | Cys | Glu | Val | Arg | Glu | Pro | Asn | Lys | |
| 65 | | | | 70 | | | | | 75 | | | | | 80 | | |
| aag | tcg | cgc | atc | tgg | ctc | ggc | acc | ttc | gcc | acc | ccc | gag | gcc | gcc | gcg | 288 |
| Lys | Ser | Arg | Ile | Trp | Leu | Gly | Thr | Phe | Ala | Thr | Pro | Glu | Ala | Ala | Ala | |
| | | | | 85 | | | | | 90 | | | | | 95 | | |
| cgc | gcg | cac | gac | gtg | gcc | gcg | ctg | gcc | ctg | cgg | ggc | cgc | gcc | gcg | tgc | 336 |
| Arg | Ala | His | Asp | Val | Ala | Ala | Leu | Ala | Leu | Arg | Gly | Arg | Ala | Ala | Cys | |
| | | | 100 | | | | | 105 | | | | | 110 | | | |
| ctc | aac | ttc | gcc | gac | tcg | gcg | cgc | ctg | ctc | cag | gtc | gac | ccc | gcc | acg | 384 |
| Leu | Asn | Phe | Ala | Asp | Ser | Ala | Arg | Leu | Leu | Gln | Val | Asp | Pro | Ala | Thr | |
| | | 115 | | | | | 120 | | | | | 125 | | | | |
| ctc | gcc | acc | ccc | gac | gac | atc | cgc | cgc | gcc | gcc | atc | cag | ctc | gcc | gac | 432 |
| Leu | Ala | Thr | Pro | Asp | Asp | Ile | Arg | Arg | Ala | Ala | Ile | Gln | Leu | Ala | Asp | |
| 130 | | | | | 135 | | | | | 140 | | | | | | |
| gcc | gcc | tcg | cag | cag | gat | gag | act | gcc | gcc | gtt | gcc | gct | gac | gtg | gtc | 480 |
| Ala | Ala | Ser | Gln | Gln | Asp | Glu | Thr | Ala | Ala | Val | Ala | Ala | Asp | Val | Val | |
| 145 | | | | | 150 | | | | | 155 | | | | | 160 | |
| gcg | ccc | tcg | cag | gcg | gac | gac | gtc | gcc | gcc | gcc | gcc | gcc | gcg | gcg | gcg | 528 |
| Ala | Pro | Ser | Gln | Ala | Asp | Asp | Val | Ala | Ala | Ala | Ala | Ala | Ala | Ala | Ala | |
| | | | | 165 | | | | | 170 | | | | | 175 | | |
| gcg | atg | tac | ggc | ggc | ggc | atg | gag | ttc | gac | cac | tcg | tat | tgc | tac | gac | 576 |
| Ala | Met | Tyr | Gly | Gly | Gly | Met | Glu | Phe | Asp | His | Ser | Tyr | Cys | Tyr | Asp | |
| | | | 180 | | | | | 185 | | | | | 190 | | | |
| gac | ggg | atg | gtg | agc | ggg | agc | agc | gac | tgc | tgg | caa | agc | ggc | gcc | ggc | 624 |
| Asp | Gly | Met | Val | Ser | Gly | Ser | Ser | Asp | Cys | Trp | Gln | Ser | Gly | Ala | Gly | |
| | | 195 | | | | | 200 | | | | | 205 | | | | |
| gcc | ggt | gga | tgg | cat | agc | atc | gtg | gac | ggc | gac | tac | gac | gac | ggc | gcc | 672 |
| Ala | Gly | Gly | Trp | His | Ser | Ile | Val | Asp | Gly | Asp | Tyr | Asp | Asp | Gly | Ala | |
| 210 | | | | | 215 | | | | | 220 | | | | | | |
| agc | gac | atg | acg | ctc | tgg | agc | tac | tga | | | | | | | | 699 |
| Ser | Asp | Met | Thr | Leu | Trp | Ser | Tyr | | | | | | | | | |
| 225 | | | | | 230 | | | | | | | | | | | |

```
<210> SEQ ID NO 4
<211> LENGTH: 232
<212> TYPE: PRT
<213> ORGANISM: Zea mays
```

<400> SEQUENCE: 4

```
Met Glu Tyr Ala Ala Val Gly Tyr Gly Tyr Gly Tyr Gly Tyr Asp Glu
 1               5                  10                  15
Arg Gln Glu Pro Ala Glu Ser Ala Asp Gly Gly Gly Gly Asp Asp
            20                  25                  30
Glu Tyr Ala Thr Val Leu Ser Ala Pro Pro Lys Arg Pro Ala Gly Arg
                35                  40                  45
Thr Lys Phe Arg Glu Thr Arg His Pro Val Tyr Arg Gly Val Arg Arg
    50                  55                  60
Arg Gly Pro Ala Gly Arg Trp Val Cys Glu Val Arg Glu Pro Asn Lys
65                  70                  75                  80
Lys Ser Arg Ile Trp Leu Gly Thr Phe Ala Thr Pro Glu Ala Ala Ala
                85                  90                  95
Arg Ala His Asp Val Ala Ala Leu Ala Leu Arg Gly Arg Ala Ala Cys
                100                 105                 110
Leu Asn Phe Ala Asp Ser Ala Arg Leu Leu Gln Val Asp Pro Ala Thr
            115                 120                 125
Leu Ala Thr Pro Asp Asp Ile Arg Arg Ala Ala Ile Gln Leu Ala Asp
    130                 135                 140
Ala Ala Ser Gln Gln Asp Glu Thr Ala Ala Val Ala Ala Asp Val Val
145                 150                 155                 160
Ala Pro Ser Gln Ala Asp Asp Val Ala Ala Ala Ala Ala Ala Ala Ala
                165                 170                 175
Ala Met Tyr Gly Gly Met Glu Phe Asp His Ser Tyr Cys Tyr Asp
                180                 185                 190
Asp Gly Met Val Ser Gly Ser Ser Asp Cys Trp Gln Ser Gly Ala Gly
            195                 200                 205
Ala Gly Gly Trp His Ser Ile Val Asp Gly Asp Tyr Asp Asp Gly Ala
    210                 215                 220
Ser Asp Met Thr Leu Trp Ser Tyr
225                 230
```

<210> SEQ ID NO 5
<211> LENGTH: 615
<212> TYPE: DNA
<213> ORGANISM: Zea mays
<220> FEATURE:
<221> NAME/KEY: promoter
<222> LOCATION: (1)...(615)
<223> OTHER INFORMATION: rab17
<220> FEATURE:
<221> NAME/KEY: misc_binding
<222> LOCATION: (233)...(238)
<223> OTHER INFORMATION: CRT/DRE
<220> FEATURE:
<221> NAME/KEY: misc_binding
<222> LOCATION: (322)...(327)
<223> OTHER INFORMATION: CRT/DRE

<400> SEQUENCE: 5

```
ctatagtatt taaaattgc attaacaaac atgtcctaat tggtactcct gagatactat      60
accctcctgt tttaaaatag ttggcattat cgaattatca ttttactttt taatgttttc    120
tcttctttta atatatttta tgaattttaa tgtatttaa aatgttatgc agttcgctct     180
ggacttttct gctgcgccta cacttgggtg tactgggcct aaattcagcc tgaccgaccg    240
cctgcattga ataatggatg agcaccggta aaatccgcgt acccaacttt cgagaagaac    300
cgagacgtgg cgggccgggc caccgacgca cggcaccagc gactgcacac gtcccgccgg    360
```

-continued

```
cgtacgtgta cgtgctgttc cctcactggc cgcccaatcc actcatgcat gcccacgtac      420 accctgccg tggcgcgccc agatcctaat cctttcgccg ttctgcactt ctgctgccta       480
taaatggcgg catcgaccgt cacctgcttc accaccggcg agccacatcg agaacacgat      540
cgagcacaca agcacgaaga ctcgtttagg agaaaccaca aaccaccaag ccgtgcaagc      600
accatggacg ccgcc                                                       615
```

<210> SEQ ID NO 6
<211> LENGTH: 1625
<212> TYPE: DNA
<213> ORGANISM: Arabidopsis
<220> FEATURE:
<221> NAME/KEY: promoter
<222> LOCATION: (1)...(1625)
<223> OTHER INFORMATION: rd29A
<220> FEATURE:
<221> NAME/KEY: misc_binding
<222> LOCATION: (1323)...(1328)
<223> OTHER INFORMATION: CRT/DRE

<400> SEQUENCE: 6

```
agcttggttg ctatggtagg gactatgggg ttttcggatt ccggtggaag tgagtgggga      60
ggcagtggcg gaggtaaggg agttcaagat tctggaactg aagatttggg gttttgcttt     120
tgaatgtttg cgttttttgta tgatgcctct gtttgtgaac tttgatgtat tttatctttg    180
tgtgaaaaag agattgggtt aataaaatat ttgcttttttt ggataagaaa ctcttttagc    240
ggcccattaa taaaggttac aaatgcaaaa tcatgttagc gtcagatatt taattattcg    300
aagatgattg tgatagattt aaaattatcc tagtcaaaaa gaaagagtag gttgagcaga    360
aacagtgaca tctgttgttt gtaccataca aattagttta gattattggt taacatgtta    420
aatggctatg catgtgacat ttagacctta tcggaattaa tttgtagaat tattaattaa    480
gatgttgatt agttcaaaca aaatttttat attaaaaat gtaaacgaat attttgtatg     540
ttcagtgaaa gtaaaacaaa ttaaattaac aagaaactta tagaagaaaa tttttactat    600
ttaagagaaa gaaaaaaatc tatcatttaa tctgagtcct aaaaactgtt atacttaaca    660
gttaacgcat gatttgatgg aggagccata gatgcaattc aatcaaactg aaatttctgc    720
aagaatctca aacacggaga tctcaaagtt gaaagaaaa tttatttctt cgactcaaaa     780
caaacttacg aaatttaggt agaacttata tacattatat tgtaattttt tgtaacaaaa    840 tgttttttatt attattatag aattttactg gttaaattaa aaatgaatag aaaaggtgaa    900
ttaagaggag agaggaggta acatttctt tctattttt catattttca ggataaatta     960
ttgtaaaagt ttacaagatt tccatttgac tagtgtaaat gaggaatatt ctctagtaag   1020
atcattattt catctacttc ttttatcttc taccagtaga ggaataaaca atatttagct   1080
cctttgtaaa tacaaattaa ttttccttct tgacatcatt caattttaat tttacgtata   1140
aaataaaaga tcatacctat tagaacgatt aaggagaaat acaattcgaa tgagaaggat   1200
gtgccgtttg ttataataaa cagccacacg acgtaaacgt aaaatgacca catgatgggc   1260
caatagacat ggaccgacta ctaataatag taagttacat tttaggatgg aataaatatc   1320
ataccgacat cagttttgaa agaaaaggga aaaaagaaa aataaataa aagatatact    1380 accgacatga gttccaaaaa gcaaaaaaaa agatcaagcc gacacagaca cgcgtagaga   1440
gcaaaatgac tttgacgtca caccacgaaa acagacgctt catacgtgtc cctttatctc   1500
tctcagtctc tctataaact tagtgagacc ctcctctgtt ttactcacaa atatgcaaac   1560
```

-continued

```
tagaaaacaa tcatcaggaa taaagggttt gattacttct attggaaaga aaaaaatctt    1620
tggac                                                               1625

<210> SEQ ID NO 7
<211> LENGTH: 1824
<212> TYPE: DNA
<213> ORGANISM: Zea mays
<220> FEATURE:
<221> NAME/KEY: promoter
<222> LOCATION: (1)...(1824)
<223> OTHER INFORMATION: RIP2
<220> FEATURE:
<221> NAME/KEY: misc_binding
<222> LOCATION: (1653)...(1658)
<223> OTHER INFORMATION: CRT/DRE

<400> SEQUENCE: 7
taatcattac ttaggtttta ttttaccaca tttttatttt gttttcccct gttccttttc      60
tcttcatttc cattcaatta atgggatgtt tgatacctta cgattgcacc aacctgttca    120
attgtacttc agatatcatc ttctttgatt gtctctcacc tctgctttgc ttcagtacct    180
gtattttttc ccatgaccct gaattctatt tgcccacatc acaacacttg cttcttctcg    240
aacaaataaa taaacaaact tcacagaacc gtagttttta tttctatcca tacattgtca    300
gtttgatgat ccagacgagg tagatgaaga gaaagaagtt gagtatgaag aaatcgagga    360
ggaggttgag tatgaagaga tagaggagga ttaagaaatt gatggtgtgt gtgaatttga    420
tgctaatgat gaaagtaaaa tggtcgatgt tgatgcgaat gatgagaatg aaaaacggaa    480
gcatgctgag cttcttgctc ttactcatgg agctgaagtt tatgttgggg catatcttct    540
aatgtatctt ctgaaaatct caaacaacta ttctgaagat ctcaaacaac tatttgaatc    600
tgttgggagc tgaagtttat gttgggcata tcttctgatg tatcttctct actttagctt    660
ttgcatttct attctctgca aatttagagt cccttttttct gcaggttgta tatccttatt    720
gtgtcgcatg ttttggccga tgctacccga attgggcaac aatgatctca gaatgtcatg    780
acacacattt gacattgtcc atctactatt gatcgtgcct gcaagattga acagatcaag    840 cttttgaaaga aggatgtcaa aaggcattgg tgattgaaca aaggcagtca agagccattg    900
aaagaaagtt gtatgttgag agcactaaga caacggtctt acagtgtaca aaatatatca    960
ctgaatagtt atatcttact tttttagcac ttgagcaatt aaacttttag ttgttcattg   1020
ttatagtcga tacccagata tcatacagtg tctaatatga acatttaatt ttcatgtaat   1080
cattatgctc taacattttt taaaaaataa tgtgctgttg caacgcacgg gcatcgtact   1140
agtaaagtat atatatatat atatatatat agacttttac cattcaaaaa aatttgaggg   1200
cctcaatttt ttgtttcgcc ccgggtccat gaaacctagg gaccggccgt gtatatatat   1260
ggtcttccct tcactaacta tatagagaca gatcacatcg gaataaaaga aatttataga   1320
ccaaatcgga aacctaaaaa ccaaaaaccg agcaattcgg tctattcggt tttagttagc   1380
aggttcaaaa tgtccggtcc tactaatact caacaatgat taagaaccga tctgccatat   1440
tttaaaaaat tatggaccgg aataacacat agtgaaaagt ttaaggagcg aaaatatttt   1500
tttttccttg gcaatttgga cggcacgcgg agactggcag accgcatcct cgtgaagcac   1560
gttgtccatg cctgaagaga gtattctgta ttcgcagtat tcctgcattt aaagtttgg    1620 tgagcgaatc aataattggc ataaataatg ctaccgacgc atcaccacat agtacgtacc   1680
atagtcatcc ttatcctatc gaattaccta catgcccaac cctcccacta catatatctg   1740
caacgagcgc atcgccaatt cacaatgcca attgccagca acccatccat actttcagct   1800
```
gttgatacaa aaagagaaga gaga                                              1824

<210> SEQ ID NO 8
<211> LENGTH: 1099
<212> TYPE: DNA
<213> ORGANISM: Zea mays
<220> FEATURE:
<221> NAME/KEY: promoter
<222> LOCATION: (1)...(1099)
<223> OTHER INFORMATION: RIP2
<220> FEATURE:
<221> NAME/KEY: misc_binding
<222> LOCATION: (930)...(935)
<223> OTHER INFORMATION: CRT/DRE

<400> SEQUENCE: 8
gcccttgttt tggccgatgc tacccgaatt gggcaacaat gatctcagaa tgtcatgaca      60
cacatttgac attgtccatc tactattgat cgtgcctgca agattgaaca gatcaagctt     120
tgaaagaagg atgtcaaaag gcattggtga ttgaacaaag gcagtcaaga gccattgaaa     180
gaaagttgta tgttgagagc actaagacaa cggtcttaca gtgtacaaaa tatatcactg     240
aatagttata tcttactttt ttagcacttg agcaattaaa cttttagttg ttcattgtta     300
tagtcgatac ccagatatca tacagtgtct aatatgaaca tttaattttc atgtaatcat     360
tatgctctaa catttttaa aaaataatgt gctgttgcaa cgcacgggca tcgtactagt     420
aaagtatata tatatatata tatatataga cttttaccat tcaaaaaaat ttgagggcct     480
caattttttg tttcgccccg ggtccatgaa acctaggac cggccgtgta tatatatggt     540
cttcccttca ctaactatat agagacagat cacatcggaa taaaagaaat ttatagacca     600
aatcggaaac ctaaaaacca aaaaccgagc aattcggtct attcggtttt agttagcagg     660
ttcaaaatgt ccggtcctac taatactcaa caatgattaa gaaccgatct gccatatttt     720
aaaaaattat ggaccggaat aacacatagt gaaaagttta aggagcgaaa atatttttt     780
ttccttggca atttggacgg cacgcggaga ctggcagacc gcatcctcgt gaagcacgtt     840
gtccatgcct gaagagagta ttctgtattc gcagtattcc tgcatttaaa agtttggtga     900
gcgaatcaat aattggcata ataatgcta ccgacgcatc accacatagt acgtaccata     960
gtcatcctta tcctatcgaa ttacctacat gcccaaccct cccactacat atatctgcaa    1020
cgagcgcatc gccaattcac aatgccaatt gccagcaacc catccatact ttcagctgtt    1080
gatacaaaaa gagaagaga                                                 1099

<210> SEQ ID NO 9
<211> LENGTH: 1446
<212> TYPE: DNA
<213> ORGANISM: Zea mays
<220> FEATURE:
<221> NAME/KEY: promoter
<222> LOCATION: (1)...(1443)
<223> OTHER INFORMATION: mLIP15
<220> FEATURE:
<221> NAME/KEY: misc_binding
<222> LOCATION: (706)...(710)
<223> OTHER INFORMATION: CRT/DRE
<220> FEATURE:
<221> NAME/KEY: misc_binding
<222> LOCATION: (1426)...(1430)
<223> OTHER INFORMATION: CRT/DRE
<220> FEATURE:
<221> NAME/KEY: misc_feature
<222> LOCATION: 1366, 1374
<223> OTHER INFORMATION: n = A,T,C or G -continued

```
<400> SEQUENCE: 9
aagcttggta ccgagctcgg atccactagt aacggccgcc agtgtgctgg aattcgccct      60
tctgggcaag ctgtcactag gactggacaa atactcgtg gctcgataac tcgctcgact      120
cgtctcgtta gtagctcagc tcgactcggc tcgttttaat tttgtagcga gccaagctag      180
cattctagct cgattctcta atgagccagc tcggttagc tcgtgagcta gctcgcgagc      240
caaacgagct aagccacaac acaaatttgt ctagtcattg atgtcgtctc atctctcata      300
gtcttgtttt ctcgtagtta tgatctgtga tatggacatg tgtggatgtg ccatgtactt      360
aaatatttat attattgcat ggctacatgt ttgtagtgtt aaatacttaa aatataattt      420
ttcggttata aatatattta tgtacataga tatttatatt tagttgtgtg gctcacgagc      480
ctaacgagct ggctcgagct tcctaacgag ccgagccgag ccagctgttt agcccgttag      540
tataacgagc cgagccgagc tggctcgtta gtaacgag tcataacgag ccgagccata      600
acgagccaag ctggttcgat atccacccct agctgtcacc gtcgcccagt ccgcttcgtt      660
cggtcagcgg gccccgcctc atctgcattc ttccattctc gtcctccgac ctcatctgca      720
ttttcccagc caagtagtag gtaaactagt ggcggtcccg tggccgtggc atcaggaaaa      780
gaatatgccg tcccagccca ccatcccccc accgtcccga aattcaagag ttaccttggg      840
ttcaagttat aataggctgc cccggtaga cgttggaaac tttccccttc tcgggataaa      900
agataaggag tgtgtgtcct ttttttagga taagtccgtg cccccttctgt ttttcttaca      960 ttcaggtctt cgcagctcct ctattttttg ttgtttcttt ctttcgatct gcagccgtg     1020 caggtccagt actctccttt ctgtgaagga actcttgcag ccggcccctc tggtttcgtc     1080
gaattcttgt tccccggtcc ctcctcctgt ccccgcgtag atccgtccgt ccgaggagca     1140
caccgtcccc accccatgt ttacccacca gttcctctga cggccgccgt gctccgatga     1200
agatgagcgt gctccgtatc cgccgctccc actccttctc cgtcgccttc ctctactggt     1260
tctacgtctt ctcatgaacg catcgcccct ctccacctgc tgatccttcg ccgtctctct     1320
ctctctctct ctctctctct cttagatagt cttttgaatc catctntagg gctnttgttt     1380
ctccccatcc tccccccacc ccaccccccca ccaaacagat tcaatccgac aagacaagca     1440
tccatg                                                                1446

<210> SEQ ID NO 10
<211> LENGTH: 781
<212> TYPE: DNA
<213> ORGANISM: Secale cereale

<400> SEQUENCE: 10
catggacgcc gccgacgccg gctcccccg ttttgggcac aggacggtgt gctcggagcc      60
gcccaagagg ccggcagggc ggaccaagtt taaggagacc cgccaccgc tgtaccgcgg     120 cgtgcggcgg cgggtcggc tcgggcagtg ggtgtgcgag gtgcgcgtgc gcggcgcgca     180
agggtacagg ctctggctcg gcacattcac caccgccgag atggcggcgc gcgcgcacga     240
ctccgccgtg ctcgcgctcc tcgaccgcgc cgcttgcctc aacttcgccg actccgcctg     300
gcggatgctg cccgtcctcg cggcaggctc gtcccgcttc agcagcgcgc gggaaatcaa     360
ggacgccgtc gccgtcgccg tcgtggagtt ccagcggcag cgcccttcg tgtccacgtc     420 ggagacggcc gacggcgaga aggacgtcca aggctcgccg aggccgagcg agctgtccac     480
gtccagcgac ttgttggacg agcactggtt tagcggcatg gacgccggct cttactacgc     540
gagcttggcg caggggatgc tcatggagcc gccggccgcc agagcgtgga gcgaggatgg     600
```

-continued

```
cggcgaatac agcggcgtcc acacgccgct ttggaactag tactagtaca cttatccgac      660
taattaagcc atgtacagtt ttagaaacta gactactagt ggttgtgttc ttccaaatat      720
gggaagatac agagtaagca taaggagcaa ttttcccccg taaaaaaaaa aaaaaagggg      780
c                                                                     781

<210> SEQ ID NO 11
<211> LENGTH: 902
<212> TYPE: DNA
<213> ORGANISM: Arabidopsis thaliana
<220> FEATURE:
<221> NAME/KEY: CDS
<222> LOCATION: (113)...(763)

<400> SEQUENCE: 11
ctagaacaga aagagagaga aactattatt tcagcaaacc ataccaacaa aaaagacaga      60
gatcttttag ttaccttatc cagtttcttg aaacagagta ctcttctgat ca atg aac     118
                                                         Met Asn
                                                           1 tca ttt tct gct ttt tct gaa atg ttt ggc tcc gat tac gag tct tcg       166
Ser Phe Ser Ala Phe Ser Glu Met Phe Gly Ser Asp Tyr Glu Ser Ser
         5                  10                  15 gtt tcc tca ggc ggt gat tat att ccg acg ctt gcg agc agc tgc ccc       214
Val Ser Ser Gly Gly Asp Tyr Ile Pro Thr Leu Ala Ser Ser Cys Pro
 20                  25                  30 aag aaa ccg gcg ggt cgt aag aag ttt cgt gag act cgt cac cca ata       262
Lys Lys Pro Ala Gly Arg Lys Lys Phe Arg Glu Thr Arg His Pro Ile
 35                  40                  45                  50 tac aga gga gtt cgt cgg aga aac tcc ggt aag tgg gtt tgt gag gtt       310
Tyr Arg Gly Val Arg Arg Arg Asn Ser Gly Lys Trp Val Cys Glu Val
                 55                  60                  65 aga gaa cca aac aag aaa aca agg att tgg ctc gga aca ttt caa acc       358
Arg Glu Pro Asn Lys Lys Thr Arg Ile Trp Leu Gly Thr Phe Gln Thr
             70                  75                  80 gct gag atg gca gct cga gct cac gac gtt gcc gct tta gcc ctt cgt       406
Ala Glu Met Ala Ala Arg Ala His Asp Val Ala Ala Leu Ala Leu Arg
         85                  90                  95 ggc cga tca gcc tgt ctc aat ttc gct gac tcg gct tgg aga ctc cga       454
Gly Arg Ser Ala Cys Leu Asn Phe Ala Asp Ser Ala Trp Arg Leu Arg
100                 105                 110 atc ccg gaa tca act tgc gct aag gac atc caa aag gcg gcg gct gaa       502
Ile Pro Glu Ser Thr Cys Ala Lys Asp Ile Gln Lys Ala Ala Ala Glu
115                 120                 125                 130 gct gcg ttg gcg ttt cag gat gag atg tgt gat gcg acg acg gat cat       550
Ala Ala Leu Ala Phe Gln Asp Glu Met Cys Asp Ala Thr Thr Asp His
                135                 140                 145 ggc ttc gac atg gag gag acg ttg gtg gag gct att tac acg gcg gaa       598
Gly Phe Asp Met Glu Glu Thr Leu Val Glu Ala Ile Tyr Thr Ala Glu
            150                 155                 160 cag agc gaa aat gcg ttt tat atg cac gat gag gcg atg ttt gag atg       646
Gln Ser Glu Asn Ala Phe Tyr Met His Asp Glu Ala Met Phe Glu Met
        165                 170                 175 ccg agt ttg ttg gct aat atg gca gaa ggg atg ctt ttg ccg ctt ccg       694
Pro Ser Leu Leu Ala Asn Met Ala Glu Gly Met Leu Leu Pro Leu Pro
    180                 185                 190 tcc gta cag tgg aat cat aat cat gaa gtc gac ggc gat gat gac gac       742
Ser Val Gln Trp Asn His Asn His Glu Val Asp Gly Asp Asp Asp Asp
195                 200                 205                 210 gta tcg tta tgg agt tat taa aactcagatt attatttcca tttttagtac         793
```

```
Val Ser Leu Trp Ser Tyr  *
                215 gatactttt atttattat tatttttaga tccttttta gaatggaatc ttcattatgt      853
ttgtaaaact gagaaacgag tgtaaattaa attgattcag tttcagtat               902
```

<210> SEQ ID NO 12
<211> LENGTH: 216
<212> TYPE: PRT
<213> ORGANISM: Arabidopsis thaliana

<400> SEQUENCE: 12

```
Met Asn Ser Phe Ser Ala Phe Ser Glu Met Phe Gly Ser Asp Tyr Glu
 1               5                  10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg His
            35                  40                  45

Pro Ile Tyr Arg Gly Val Arg Arg Arg Asn Ser Gly Lys Trp Val Cys
50                  55                  60

Glu Val Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
                100                 105                 110

Leu Arg Ile Pro Glu Ser Thr Cys Ala Lys Asp Ile Gln Lys Ala Ala
                115                 120                 125

Ala Glu Ala Ala Leu Ala Phe Gln Asp Glu Met Cys Asp Ala Thr Thr
130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
                180                 185                 190

Leu Pro Ser Val Gln Trp Asn His Asn His Glu Val Asp Gly Asp Asp
                195                 200                 205

Asp Asp Val Ser Leu Trp Ser Tyr
210                 215
```